(12) United States Patent
Wang et al.

(10) Patent No.: US 10,987,153 B2
(45) Date of Patent: Apr. 27, 2021

(54) FORCEPS WITH ACTIVE JAW ENTRAPMENT OF TISSUE

(71) Applicant: Gyrus ACMI, Inc., Southborough, MA (US)

(72) Inventors: Huisun Wang, Maple Grove, MN (US); Kester J. Batchelor, Mound, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 165 days.

(21) Appl. No.: 15/865,893

(22) Filed: Jan. 9, 2018

(65) Prior Publication Data

US 2018/0199985 A1 Jul. 19, 2018

Related U.S. Application Data

(60) Provisional application No. 62/446,617, filed on Jan. 16, 2017, provisional application No. 62/453,702, filed on Feb. 2, 2017.

(51) Int. Cl.
| | | |
|---|---|---|
| *A61B 18/08* | (2006.01) |
| *A61B 17/29* | (2006.01) |
| *A61B 18/14* | (2006.01) |
| *A61B 17/00* | (2006.01) |
| *A61B 17/32* | (2006.01) |
| *A61B 18/00* | (2006.01) |
| *A61B 17/28* | (2006.01) |

(52) U.S. Cl.
CPC ............ *A61B 18/085* (2013.01); *A61B 17/29* (2013.01); *A61B 18/1442* (2013.01); *A61B 18/1445* (2013.01); *A61B 17/320016* (2013.01); *A61B 2017/00353* (2013.01); *A61B 2017/2825* (2013.01); *A61B 2017/2926* (2013.01); *A61B 2017/2944* (2013.01); *A61B 2017/320064* (2013.01); *A61B 2018/00577* (2013.01); *A61B 2018/00589* (2013.01); *A61B 2018/00595* (2013.01)

(58) Field of Classification Search
CPC ............ A61B 17/29; A61B 17/320016; A61B 18/085; A61B 18/1442; A61B 18/1445; A61B 2017/00353; A61B 2017/2825; A61B 2017/2926; A61B 2017/2944; A61B 2017/320064; A61B 2018/00577; A61B 2018/00589; A61B 2018/00595
See application file for complete search history.

(56) References Cited

U.S. PATENT DOCUMENTS

| | | |
|---|---|---|
| 3,263,535 A | 8/1966 | Zurcher |
| 3,575,038 A | 4/1971 | Mallett |
| 5,410,903 A | 5/1995 | Schneider |
| 5,520,704 A | 5/1996 | Castro et al. |
| 5,863,033 A | 1/1999 | Bradford |
| 6,000,686 A | 12/1999 | Yates |

(Continued)

*Primary Examiner* — Kathleen S Holwerda
*Assistant Examiner* — Brooke Labranche
(74) *Attorney, Agent, or Firm* — Schwegman Lundberg & Woessner, P.A,

(57) ABSTRACT

An end effector assembly includes a first jaw and a second jaw, at least one of which is moveable between an open positon and a closed position, a third jaw that is carried on and translates along the first jaw, and a third jaw closing mechanism that brings the third jaw into a position approximating the first jaw.

16 Claims, 3 Drawing Sheets

(56) References Cited

U.S. PATENT DOCUMENTS

| | | | |
|---|---|---|---|
| 6,527,786 B1 | 3/2003 | Davis et al. | |
| 8,075,558 B2 | 12/2011 | Truckai et al. | |
| 8,870,902 B2 * | 10/2014 | Deodhar | A61B 17/295 |
| | | | 606/174 |
| 8,974,479 B2 * | 3/2015 | Ross | A61B 17/320092 |
| | | | 606/169 |
| 9,375,266 B2 * | 6/2016 | Twomey | A61B 18/1445 |
| 2007/0078459 A1 * | 4/2007 | Johnson | A61B 17/29 |
| | | | 606/51 |
| 2012/0303025 A1 * | 11/2012 | Garrison | A61B 17/29 |
| | | | 606/51 |

* cited by examiner

FORCEPS WITH ACTIVE JAW ENTRAPMENT OF TISSUE

RELATED APPLICATION

The present application claims the benefit of U.S. Provisional Patent Application No. 62/446,617, filed on Jan. 16, 2017, and U.S. Provisional Patent Application No. 62/453,702, filed on Feb. 2, 2017.

The contents of the above applications are incorporated herein by reference in their entirety.

FIELD

The present disclosure relates to forceps. More specifically, the present disclosure relates to forceps with active jaw entrapment of tissue.

BACKGROUND

The statements in this section merely provide background information related to the present disclosure and may not constitute prior art.

Generally, forceps may be utilized for laparoscopic surgery. The forceps may be employed to control delicate movements inside a patient and may include an assembly to grip tissue. The tissue, however, may be damaged when manipulated with devices such as hooks or other aggressive elements.

Certain devices employ articulation components to trap tissue. For example, a typical articulation component is a device with two plates with at least one plate being moveable. With such devices, however, tissue may slip out of the plates when grasped by the plates since the tissue moves in the direction where there is less pressure applied to it.

In another type of device, parallel closure jaws with teeth have been proposed to grip tissue. Unless the jaw alignment is closely controlled, however, scissoring can occur between the teeth, which cuts tissue that is supposed to be grasped atraumatically.

Accordingly, there is a need in the art for forceps that can grip tissue without damaging the tissue.

SUMMARY

The present invention provides a forceps with an active jaw mechanism to entrap tissue.

Accordingly, pursuant to one aspect of the present invention, an end effector assembly includes a first jaw and a second jaw, at least one of which is moveable between an open positon and a closed position, a third jaw that is carried on and translates along the first jaw, and a third jaw closing mechanism that brings the third jaw into a position approximating the first jaw.

The foregoing aspect of the present invention can be further characterized by one or any combination of the features described herein, such as: the first jaw is a stationary jaw; the first jaw is a moveable jaw; a region between the third jaw and the first jaw defines a capture zone; the third jaw has a gripping section with a distal face and the first jaw has a gripping section with a proximal face, the region between the distal face and the proximal face defining the capture zone; the capture zone decreases to pinch tissue located in the capture zone when the at least one jaw that is moveable moves to the closed position; the first jaw has a first set of teeth and the third jaw has a second set of teeth, the first set of teeth and the second set of teeth pinching tissue when the at least one jaw that is moveable moves to the closed position; at least one of the first jaw, the second jaw and the third jaw has a sealing surface with an electrode; the first jaw and the second jaw have a sealing surface with an electrode; and the electrode is connected to a source of electrosurgical energy, the source generating electrosurgical energy to coagulate tissue grasped between at least two of the first jaw, the second jaw and the third jaw.

Accordingly, pursuant to another aspect of the present invention, a forceps includes a first jaw and a second jaw, at least one of which is moveable between an open positon and a closed position, a third jaw that is carried on and translates along the first jaw, and a third jaw closing mechanism that brings the third jaw into a position approximating the first jaw, the third jaw closing mechanism being a mechanism that closes the third jaw against the first jaw by the closure of the at least one moveable jaw.

The foregoing aspect of the present invention can be further characterized by one or any combination of the features described herein, such as: the third jaw closing mechanism is an eccentric cam on a pivot between the first jaw and the second jaw; the third jaw closing mechanism is a push rod cam that moves the third jaw to a gripping position as the at least one moveable jaw moves to the closed position; the third jaw closing mechanism brings the third jaw into the approximating position before the at least one moveable jaw begins to move to the closed position; at least one of the first jaw, the second jaw and the third jaw has a sealing surface with an electrode, the electrode being connected to a source of electrosurgical energy to coagulate tissue grasped between at least two of the first jaw, the second jaw and the third jaw.

Accordingly, pursuant to yet another aspect of the present invention, a method of using forceps includes one or more of the following steps: opening a first jaw and a second jaw of the forceps; moving a third jaw carried on and translates along the first jaw into a position approximating the first jaw with a third jaw closure mechanism to pinch tissue between the third jaw and the first jaw; and closing the first jaw and the second jaw to grasp tissue therebetween.

The method of using the forceps may be further characterized by one or any combination of the following features: the third jaw closing mechanism is an eccentric cam on a pivot between the first jaw and the second jaw; the third jaw closing mechanism is a push rod cam that moves the third jaw to a gripping position as the at least one moveable jaw moves to the closed position; the third jaw closing mechanism brings the third jaw into the approximating position before the at least one moveable jaw begins to move to the closed position; at least one of the first jaw, the second jaw and the third jaw has a sealing surface with an electrode connected to a source of electrosurgical energy, the method further including generating electrosurgical energy with the source to coagulate tissue grasped between at least two of the first jaw, the second jaw and the third jaw.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1 is a perspective view of an end effector assembly for a forceps in accordance with the principles of the present invention;

DETAILED DESCRIPTION

Figure 1:
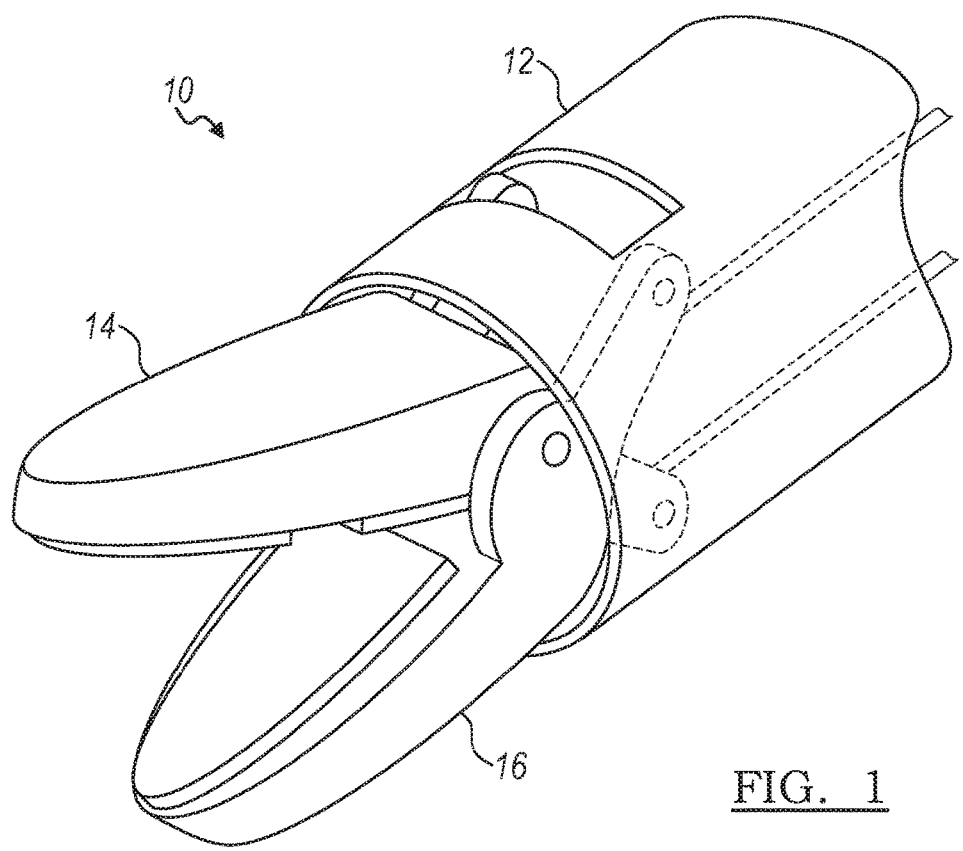

The following description is merely exemplary in nature and is not intended to limit the present disclosure, application, or uses.

Referring now to the drawings, an end effector for a forceps, such as, for example, a laparoscopic forceps, embodying the principles of the present invention is illustrated therein and designated at 10. The end effector 10 may function to grip an object. The end effector 10 may be used during surgery to grip a feature of interest including: a part of a body, an anatomical feature, tissue, veins, arteries, or a combination thereof. The end effector 10 may function to be used in surgery, for example, laparoscopic surgery. The end effector 10 may be used with or without power. Current may be passed through the end effector 10 so that the forceps are used for electrosurgery. For example, a therapy current may be passed from one jaw to a second jaw when tissue is located within the jaw and the therapy current may coagulate blood, cauterize, cut, or a combination thereof. The end effector 10 may generally include one or more working assemblies and sufficient controls to work the one or more assemblies. The end effector 10 may include parts employed to perform the recited functions and may include generally, a shaft (e.g., a tubular member, a hollow tube, or an assembly of tubes), a hand piece, one or more operable mechanisms used to actuate the shaft, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Figure 2:
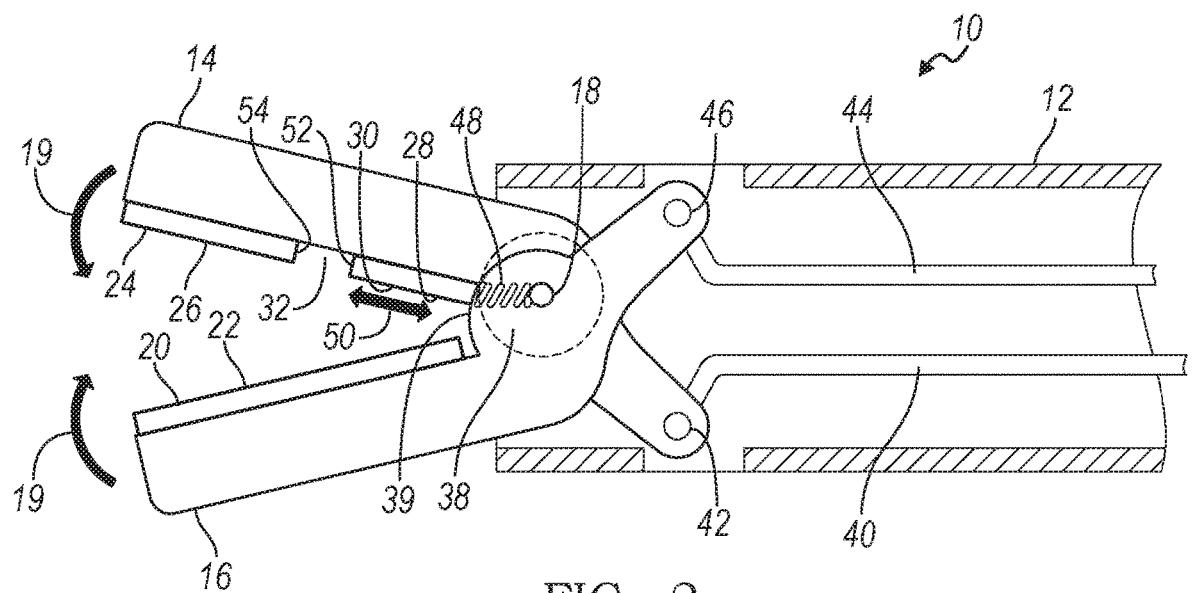
FIG. 2 is a side view an a partial cross-sectional view of the end effector assembly shown in FIG. 1.
Figure 3A:
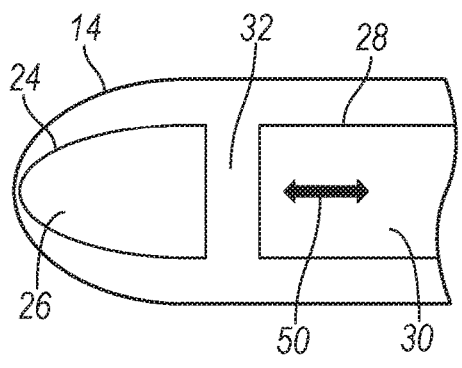
FIG. 3A is an interior view of a first jaw and a third jaw of the end effector assembly shown in FIG. 1.
Figure 3B:
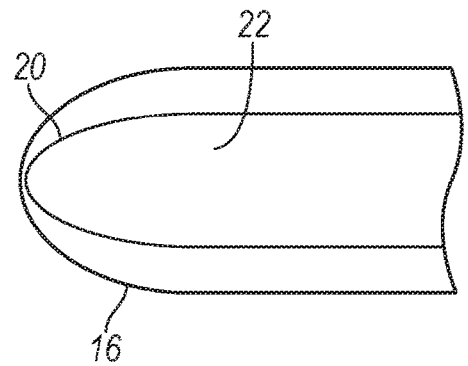
FIG. 3B is an interior view of a second jaw of the end effector assembly shown in FIG. 1.

Turning now to FIG. 1, the end effector 10 includes a first jaw 14 and a second jaw 16 partially housed in a tubular member 12. As shown in FIG. 2, a pin 18 located between the jaws holds the jaw members 14 and 16 together and provides a pivot point for the jaws 14 and 16 as the jaws 14 and 16 open and close. The fist jaw 14 is connected to a rod member 40 with a connector 42, and the second jaw 16 is connected to a rod member 44 with a connector 44. The rod members 40 and 44 extend through the tubular member 12 such that when the rod members 40 and 44 are pulled proximally (that is, towards the right in FIG. 2) the jaws 14 and 16 rotate about the pin 18 as indicated by the arrows 19 to a closed position.

The first jaw 14 includes a stationary member 24 with a sealing surface 26, and the second jaw 16 includes a stationary member 20 with a sealing surface 22. The first jaw 14 also carries a third jaw 28 with a sealing surface 30. The third jaw 28 is configured to translate along the first jaw 14 as indicated by the double-arrow 50. Specifically, the third jaw 28 is in contact with a cam member 38 of the second jaw 16. Hence, as the first jaw 14 and the second jaw 16 move to the closed position, a surface 39 of the cam member 38 pushes the third jaw 28 distally (that is, towards the left in FIG. 2.). Further note that the third jaw 28 is attached to a biasing member, such as, for example a spring 48. The spring 48, in turn, is attached to the pin 18. As such, as the third jaw 28 moves distally, a return force is applied to the third jaw 28 as the spring 48 is extended. Hence, as the first jaw 14 and the second jaw 16 are opened (that is, in the opposite direction of the arrows 19), the spring 48 pulls the third jaw 28 proximally.

As shown in FIG. 2, the third jaw 28 has a distal face 52 and the stationary member 24 of the first jaw 14 has a proximal face 54. The two faces 52 and 54 define a capture zone 32. Accordingly, as the first jaw 14 and the second jaw 16 move to the closed position as indicated by the arrows 19 to grip a vessel, V, the capture zone 32 decreases to pinch a portion, P, of the vessel, V so that the vessel, V, does not slip out distally from the first jaw 14 and the second jaw 16.

In various arrangements, any one of or all of the sealing surfaces 22 26 and 30 are electrically conductive. Accordingly, any one of the jaws 14, 16 and 28 can be electrical connected to a generator that provides a source of electrosurgical energy so that a RF voltage with different potentials can be applied to the electrically coupled sections of the jaws 14, 16 and 28. The RF voltage produces a current that passes from one jaw member to the other jaw member, thereby heating the tissue to coagulate or cut the tissue gripped between the jaws 14, 16 and 18.

Figure 5:
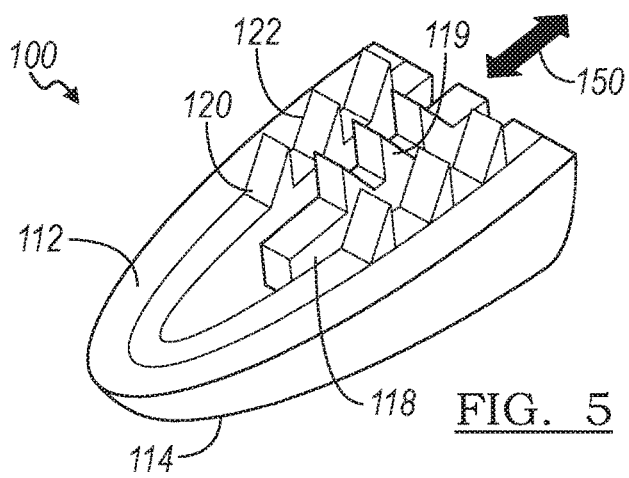
FIG. 5 is a perspective view of another end effector assembly for a forceps in accordance with the principles of the present invention.

Turning now to FIG. 5, there is shown an alternative end effector 100 that replaces the aforementioned jaw 14 with a jaw 114. The jaw 114 includes a sealing surface 112 along with a stationary set of teeth 120. A third jaw 118 is carried on the first jaw 114 and is configured to translate along the first jaw 114 as indicated by the double-arrow 150.

Figure 4:
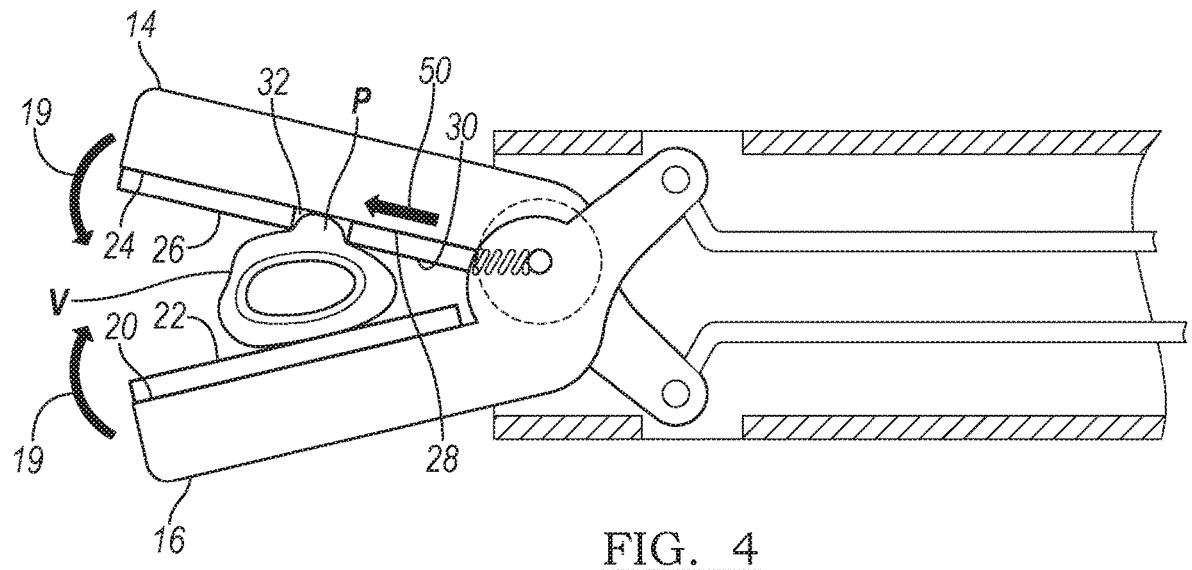
FIG. 4 is a side and partial cross-sectional view of the end effector assembly shown in FIG. 1 pinching a vessel.

In certain arrangements, the third jaw 118 is in contact with a cam member 38 such as that shown in FIGS. 2 and 4. Accordingly, as the first jaw 114 and the second jaw 16 move to a closed position, the surface 39 of the cam member 38 pushes the third jaw 118 distally. As this occurs, a portion of tissue gripped by the first jaw 114 and the second jaw 16 is pinched by teeth 119 of the third jaw 118 and teeth 122 of the first jaw 114.

Either or both the first jaw 114 and the third jaw 118 can be electrically conductive. Accordingly, any one of the jaws 16, 114 and 118 can be electrical connected to a generator that provides a source of electrosurgical energy so that a RF voltage with different potentials can be applied to the electrically connected sections of the jaws 16, 114 and 118. The RF voltage produces a current that passes from one jaw member to coagulate or cut the tissue gripped between the jaws 16, 114 and 118.

Figure 6:
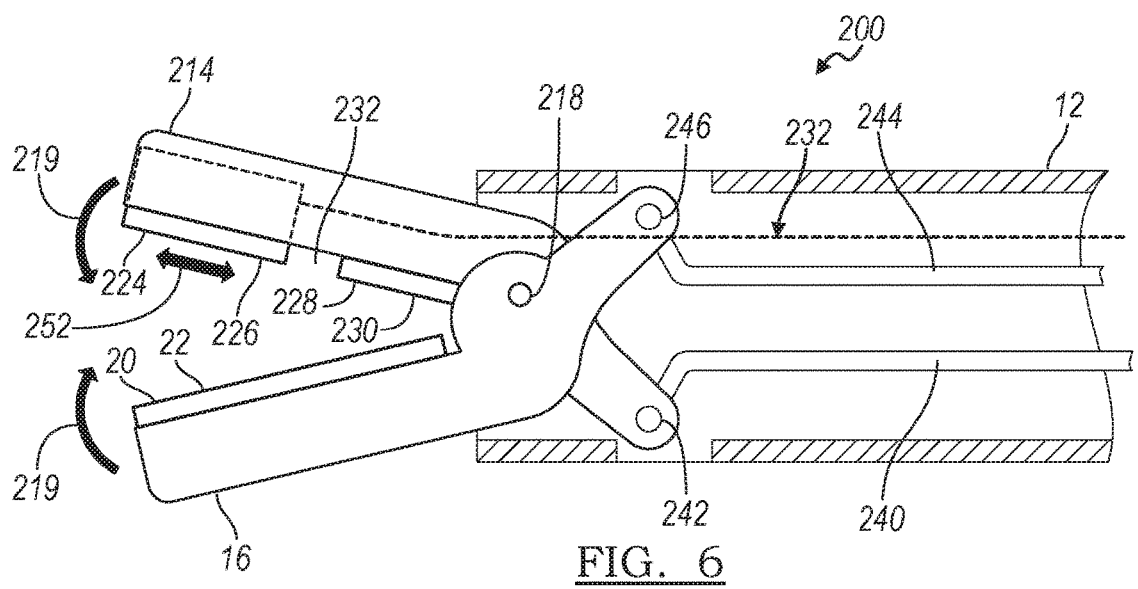
FIG. 6 is a side and partial cross-sectional view of yet another end effector assembly for a forceps in accordance with the principles of the present invention.
Figure 7:
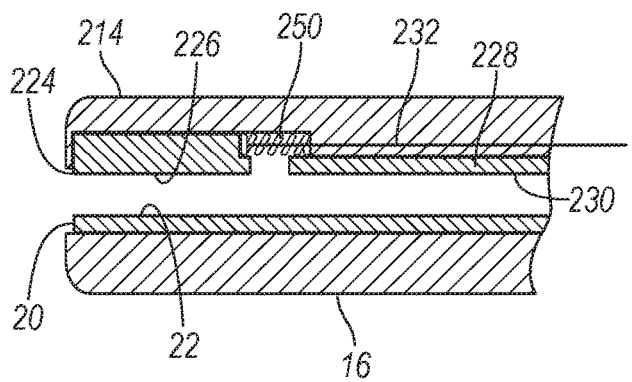
FIG. 7 is a cross-sectional view of the jaw members of the end effector assembly shown in FIG. 6.
Figure 8:
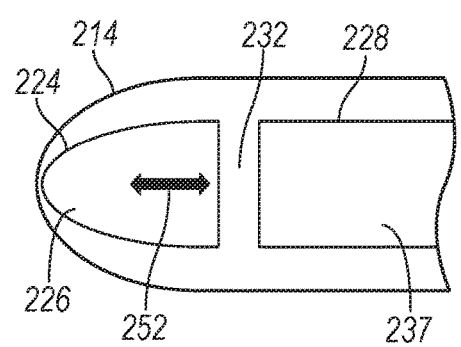
FIG. 8 is an interior view of the top jaw members shown in FIG. 7.

Referring now to FIGS. 6-8, there is shown an alternative end effector 200. The end effector 200 includes a first jaw 214 and a second jaw 216 partially housed in the tubular member 12. A pin 218 located between the jaws holds the jaw members 214 and 216 together and provides a pivot point for the jaws 214 and 216 as the jaws 214 and 216 open and close. The fist jaw 214 is connected to a rod member 240 with a connector 242, and the second jaw 216 is connected to a rod member 244 with a connector 244. The rod members 240 and 244 extend through the tubular member 12 such that when the rod members 240 and 244 are pulled proximally (that is, towards the right in FIG. 26) the jaws 214 and 216 rotate about the pin 218 as indicated by the arrows 219 to the closed position.

The first jaw 214 includes a stationary member 228 with a sealing surface 230, and the second jaw 16 is described previously. The first jaw 214 also carries a third jaw 224 with a sealing surface 226. The third jaw 224 is configured to translate along the first jaw 214 as indicated by the double-arrow 252. More specifically, the third jaw 224 is connected to a wire or rod 232 so that pulling on the rod or wire 232 moves the third jaw 224 proximally to pinch tissue in a capture zone 232 as the jaws 16 and 214 move to the closed position.

The third jaw 224 can be attached to a biasing member, such as, for example a spring 250 positioned between the first jaw 214 and the third jaw 224. In such an arrangement, as the third jaw 224 moves proximally, a return force is applied to the third jaw 224 as the spring 250 is compressed. Hence, when any tensile force is released from the wire or rod 232, the compressive force of the spring 250 moves the third jaw 224 distally.

In various arrangements, any one of or all of the sealing surfaces 22, 226 and 228 are electrically conductive. Accordingly, any one of the jaws 16, 214 and 228 can be electrical connected to a generator that provides a source of electrosurgical energy so that a RF voltage with different potentials can be applied to the electrically connected sections of the jaws 16, 214 and 228. The RF voltage produces a current that passes from one jaw member to the other jaw member, thereby heating the tissue to coagulate or cut the tissue gripped between the jaws 16, 214 and 228.

The description of the invention is merely exemplary in nature and variations that do not depart from the gist of the invention are intended to be within the scope of the invention. Such variations are not to be regarded as a departure from the spirit and scope of the invention.

What is claimed is:

1. A forceps comprising: a first jaw and a second jaw, at least one of which is moveable between an open position and a closed position, the first jaw having a first face and the second jaw having a second face that opposes the first face of the first jaw, wherein a first portion of the first face has a first sealing surface with a first electrode and a second portion of the second face has a second sealing surface with a second electrode, the first and second sealing surfaces configured to treat tissue; a third jaw that is carried on and translates along the first jaw, the third jaw being positioned between the first jaw and the second jaw, the third jaw having a third face that opposes the second face of the second jaw, the first face and the third face defining a capture zone, the capture zone being a gap between the first face and the third face; and a third jaw closing mechanism that brings the third jaw into a position approximating the first jaw, wherein the capture zone decreases to pinch tissue located in the capture zone when the at least one jaw that is moveable moves to the closed position.

2. The forceps of claim 1 wherein the first jaw is a stationary jaw.

3. The forceps of claim 1 wherein the first jaw is a moveable jaw.

4. The forceps of claim 1 wherein the third jaw has a gripping section with a distal face and the first jaw has a gripping section with a proximal face, a region between the distal face and the proximal face defining the capture zone.

5. The forceps of claim 1 wherein the first jaw has a first set of teeth and the third jaw has a second set of teeth, the first set of teeth and the second set of teeth pinching tissue when the at least one jaw that is moveable moves to the closed position.

6. The forceps of claim 1 wherein a third portion of the third face has a third sealing surface with a third electrode.

7. The forceps of claim 6 wherein at least one of the first electrode, the second electrode, and the third electrode is connected to a source of electrosurgical energy, the source generating electrosurgical energy to coagulate tissue grasped between at least two of the first jaw, the second jaw and the third jaw.

8. A forceps comprising:
   a first jaw and a second jaw, at least one of which is moveable between an open position and a closed position, the first jaw having a first face and the second jaw having a second face that opposes the first face of the first jaw; and
   a third jaw that is carried on and translates along the first jaw, the third jaw being positioned between the first jaw and the second jaw, the third jaw having a third face that opposes the second face of the second jaw, the first face and the third face defining a capture zone, the capture zone being a gap between the first face and the third face,
   wherein one of the first jaw and the second jaw includes a cam surface such that as the at least one moveable jaw closes, the third jaw interacts with the cam surface and moves into a position approximating the first jaw.

9. The forceps of claim 8 wherein the cam surface is on an eccentric cam on a pivot between the first jaw and the second jaw.

10. The forceps of claim 8 wherein at least one of the first jaw, the second jaw and the third jaw has a sealing surface with an electrode, wherein the electrode is connected to a source of electrosurgical energy, the source generating electrosurgical energy to coagulate tissue grasped between at least two of the first jaw, the second jaw and the third jaw.

11. A method of using forceps, the method comprising:
   opening a first jaw and a second jaw of the forceps, the first jaw having a first face and the second jaw having a second face that directly opposes the first face of the first jaw, wherein the first face extends longitudinally from a first end to a second end, the second end positioned distal to the first end, and wherein the second face extends longitudinally from a third end to a fourth end, the fourth end positioned distal to the third end;
   moving a third jaw that is carried on and translates along the first jaw into a position approximating the first jaw with a third jaw closure mechanism to pinch tissue between the third jaw and the first jaw, the third jaw being positioned between the first jaw and the second jaw, the third jaw having a third face extending longitudinally that directly opposes the second face of the second jaw, the first face and the third face defining a capture zone, the capture zone being a gap between the first face and the third face; and
   closing the first jaw and the second jaw to grasp tissue therebetween.

12. The method of claim 11 wherein the third jaw closure mechanism is an eccentric cam on a pivot between the first jaw and the second jaw.

13. The method of claim 11 wherein the third jaw closure mechanism is a push rod cam that moves the third jaw to a gripping position as the first jaw and the second jaw are closed.

14. The method of claim 11 wherein the third jaw closure mechanism brings the third jaw into the approximating position before the first jaw and the second jaw are closed.

15. The method of claim 11 wherein at least one of the first jaw, the second jaw and the third jaw has a sealing surface with an electrode connected to a source of electrosurgical energy, the method further comprising generating electrosurgical energy with the source to coagulate tissue grasped between at least two of the first jaw, the second jaw and the third jaw.

16. The method of claim 11, wherein moving the third jaw into the position approximating the first jaw includes:
   moving at least one of the first jaw and the second jaw such that the third jaw interacts with a cam surface on one of the first jaw and the second jaw and moves into the position approximating the first jaw.

\* \* \* \* \*